(12) United States Patent
Zaritsky et al.

(10) Patent No.: US 6,503,500 B1
(45) Date of Patent: Jan. 7, 2003

(54) BIOCONTROL AGENT CONTAINING AN ENDOTOXIN GENE

(75) Inventors: Arieh Zaritsky, Beer Sheva (IL); Sammy Boussiba, Omer (IL); Eitan Ben-Dov, Beer Sheva (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 0 days.

(21) Appl. No.: 09/147,259

(22) PCT Filed: Mar. 12, 1998

(86) PCT No.: PCT/IL98/00117

§ 371 (c)(1),
(2), (4) Date: Nov. 13, 1998

(87) PCT Pub. No.: WO98/39974

PCT Pub. Date: Sep. 17, 1998

(30) Foreign Application Priority Data

Mar. 13, 1997 (IL) .................................................. 120441

(51) Int. Cl.$^7$ .......................... A01N 63/00; C12N 1/15; C12N 1/21; C12N 15/74
(52) U.S. Cl. ................ 424/93.2; 435/252.3; 435/257.2; 435/257.1; 435/480; 514/2; 514/12
(58) Field of Search ............................ 435/252.3, 257.1, 435/257.2, 480; 424/93.2; 514/12, 2

(56) References Cited

U.S. PATENT DOCUMENTS 5,518,897 A * 5/1996 Stevens, Jr. et al. ........ 435/69.1

OTHER PUBLICATIONS

Xudong et al. High larvicidal activity of recombinant cyanobacterium Anabaena sp. PCC 7120 expressing gene 51 and gene 42 of *Bacillus sphaericus* sp. 2297. FEMS Microbiology Letters . 1993. vol. 107, pp. 247–250.*

E. Ben–Dov, et al., Journal of Bacteriology, vol. 177, No. 10, pp. 2851–2857, "Mosquito Larvicidal Activity of *Escherichia coli* with combinations of Genes from *Bacillus Thuringiensis* Subsp. Iraelensis", May, 1995.

Wu, X. et al; "Expression of Mosquitocidal *Bacillus Thuringiensis* Var. Israelensis d–endotoxin genes in filamentous cyanobacterium Anabaena Siamensis 7120", (Apr. 1996), Journal of Applied Phycology, vol. 8, p. 464.

Wu, X. et al; "Mosquito Larvicidal Activity of Transgenic Anabeana Strain PCC 7120 Expressing Combinations of Genes from *Bacillus Thuringiensis* subsp. Israelensis", (Dec. 1997), Applied and Environmental Microbiology, vol. 63, No. 12, p. 4971–4975.

Poncet S. et al; "Evaluation of synergistic Interactions Among the CryIVA, CryIVB, and CryIVD toxic Components of *B. Thuringiensis* subsp. Israelensis Crystals", (Apr. 1995), Journal of Invertebrate Pathology 66, p. 131–135.

* cited by examiner

*Primary Examiner*—Gabrielle Bugaisky
(74) *Attorney, Agent, or Firm*—Oblon, Spivak, McClelland, Maier & Neustadt, P.C.

(57) ABSTRACT

The invention provides a biocontrol agent against larvae of mosquitoes and blackflies comprising transgenic Anabaena PCC 7120 carrying a synergistic combination of the endotoxin genes CryIVA and CryIVD of *Bacillus thuringiensis* subsp. *israelensis*.

13 Claims, 2 Drawing Sheets

BIOCONTROL AGENT CONTAINING AN ENDOTOXIN GENE

FIELD OF THE INVENTION

The present invention relates to a biocontrol agent against larvae of mosquitoes and blackflies, carrying a synergistic combination of endotoxin genes of *Bacillus thuringiensis* subsp. *Israelensis*.

BACKGROUND ART

*Bacillus thuringiensis* subsp. *israelensis* has widely been used to control vectors of human infectious diseases such as mosquitoes and blackflies as described by World Health Organization. 1989 (Geographical distribution of arthropod-borne disease and their principle vectors. p. 249. In Vector Biology and Control Division, Geneva). Its larvicidal activity is contained in a parasporal crystalline inclusion synthesized during sporulation. A 75 MDa plasmid includes all the genes encoding δ-endotoxin proteins and their control elements as described by Hofte, H., (et. al. Insecticidal crystal proteins of *Bacillus thuringiensis*. Microbiol. Rev. 53:242–255, 1989). As a biological pesticide, *B. thuringiensis* subsp. *israelensis* is widely accepted because of its specificity of action towards dipteran insects and lack of effects on other organisms. In addition, it is very unlikely that mosquitoes will develop resistance to the toxin because it is composed of several proteins.

Current application of *B. thuringiensis* subsp. *israelensis* for mosquito control is limited by its short half life under field conditions. One way to overcome this limitation is by cloning the genes involved in organisms which inhabit the mosquito breeding zones. Cyanobacteria has been considered as attractive candidates for this purpose as suggested by the present inventor and others, (Genetically engineered cyanobacteria as a BTI toxin genes delivery system: a biotechnological approach to the control of malaria mosquitoes, p. 49–64, in Proceeding of Combating Malaria UNESCO Conference 1995, Paris). Several attempts have been made during the last decade to produce genetically engineered mosquitocidal cyanobacteria. Most of the work seems in favor of cloning a single cry gene in unicellular cyanobacteria, but intact transformed cells displayed mosquito larvicidal activity below the level required for effective and practical use as bioinsecticides in a natural aquatic environment as reported (Soltes-Rak, E., et. al. Effect of promoter modification on mosquitocidal CryIVB gene expression in Synechococcus sp. strain PCC 7942. Appl. Environ. Microbiol. 59:2,404–2,410, 1993). Attempts to enhance expression of cryIV genes in cyanobacteria by strong promoters (e.g., $P_{psbA}$, $P_{psbB}$) were not satisfactory, probably because the transcription or translation product is unstable there (Soltes-Rak, E., et. al. ibid.).

The presence of P20 has been claimed to raise the levels of CytA, CryIVA and CryIVD in *E. coli* and in an acrystalliferous strain of *B. thuringiensis*, probably acting as a chaperone to stabilize them. Synergism among the three purified polypeptides (CryIVA, CryIVB, and CryIVD) was clearly demonstrated as described by S. poncet, et. al. (Evaluation of synergistic interactions among the CryIVA, CryIVB, and CryIVD toxic components of *B. thuringiensis* subsp. *israelensis* crystals. J. Invertebr. Pathol. 66:131–135, 1995), with the highest rate being reported between CryIVA and CryIVD.

DISCLOSURE OF THE INVENTION

With the above state of the art in mind, a combination of CryIVA, CryIVD and p20, previously cloned and expressed in *E. coli* as an operon (in pHE4-ADR) as described by the present inventor and others (Mosquito larvicidal activity of *Escherichia coli* with combinations of genes from *Bacillus thuringiensis* sbsp. *israelensis*. J. Bacteriol. 177: 2,851–2, 857., 1995), was introduced into the nitrogen fixing filamentous Anabaena PCC 7120, and the most toxic clones selected for further studies.

In contradistinction to the results previously reported regarding attempts to enhance expression of CryIV genes in cyanobacteria it was found that there was produced a biocontrol agent having superior properties.

Thus, according to the present invention there is now provided a biocontrol agent against larvae of mosquitoes and blackflies comprising transgenic Anabaena PCC 7120 carrying a synergistic combination of the endotoxin genes CryIVA and CryIVD of *Bacillus thuringiensis* subsp. *israelensis*.

While the invention will now be described in connection with certain preferred embodiments in the following examples and with reference to the appended figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention. dr

DESCRIPTION OF PREFERRED EMBODIMENTS

Figure 1:
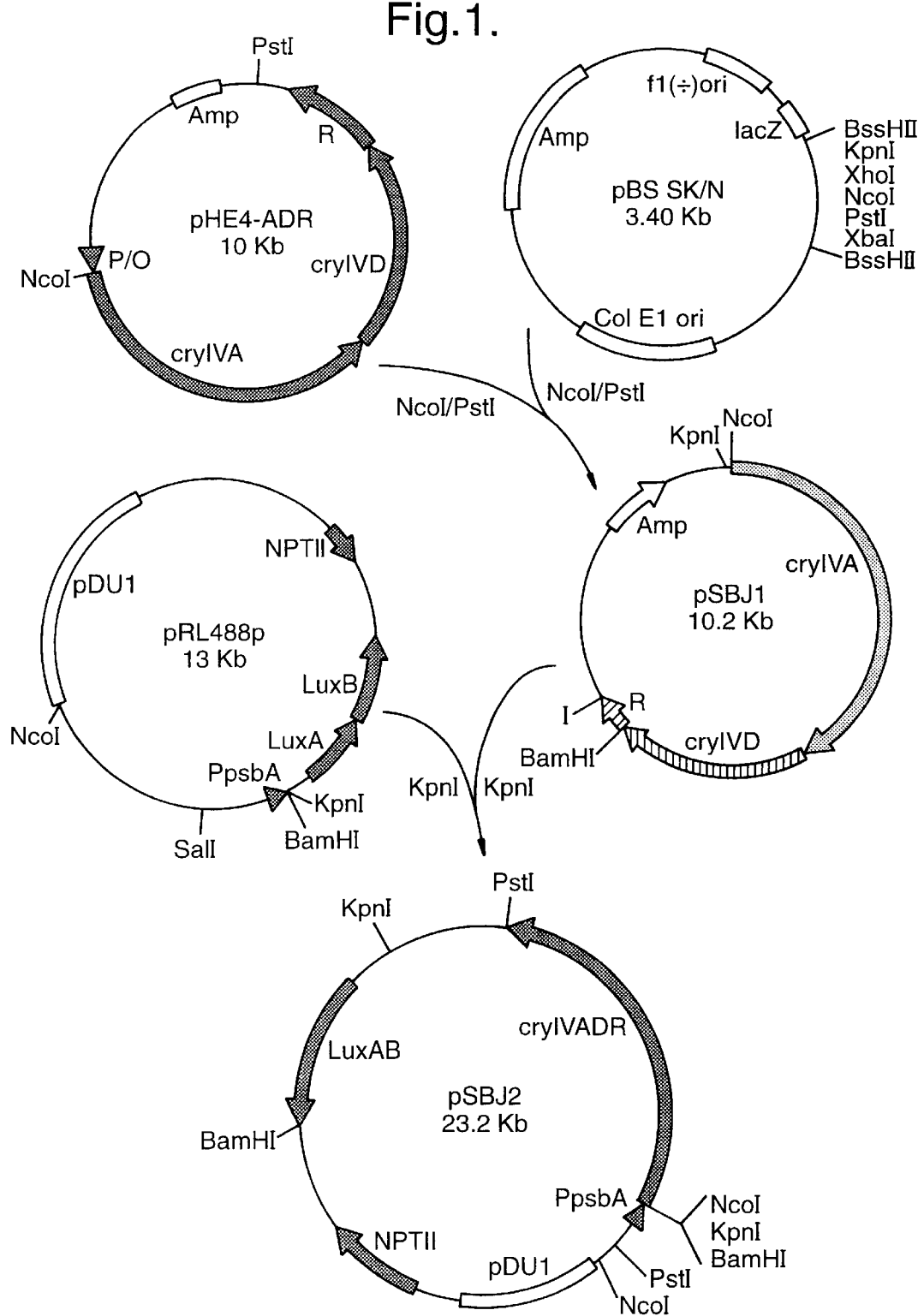
FIG. 1 illustrates the construction of a shuttle vector for expression.

More particularly, the following examples should be read in conjunction with the appended figures to which the following legend should be applied:

FIG. 1. The CryIVADR operon was transferred from pHE4-ADR(-K) into pBS=SK/N with XhoI/PstI double digestion to form pBSJ1, which was then joined with expressional shuttle vector pRL488p at its unique KpnI site. The resulting hybrid recombinant plasmid was designated as pSBJ2.

Figure 2:
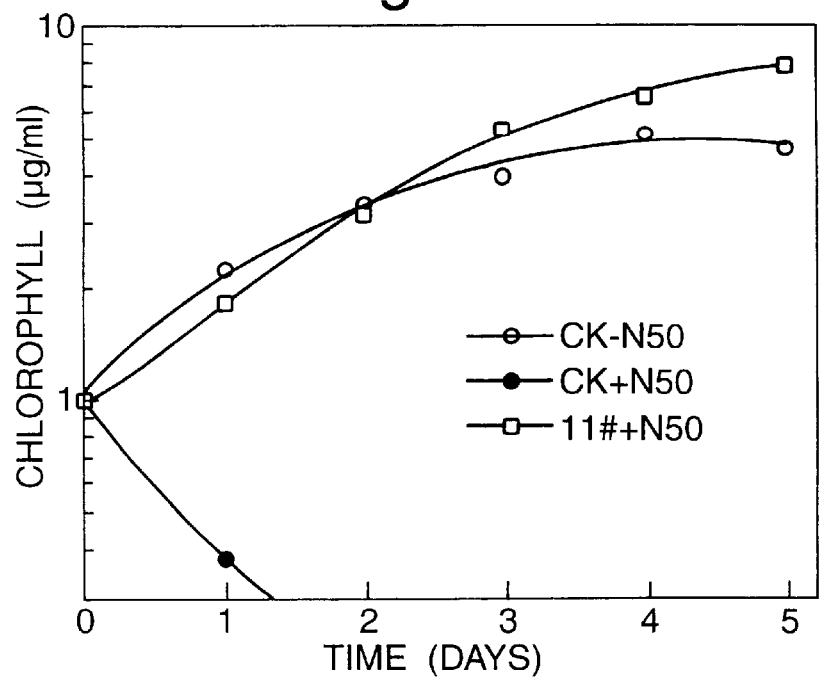
FIG. 2 graphically represents growth of exconjugant cells of Anabaena PCC 7120; and, FIG. 3 graphically illustrates toxicities of Cry1VADR expressed in cyanobacterium Anabaena PCC 7120 carrying pSBJ2.

FIG. 2. Growth of exconjugant cells of Anabaena PCC 7120 (clone #11) carrying expressional shuttle plasmid pSBJ2 in $BG_{11}$ medium. The growth conditions and chlorophyll measurements are described in the text.

Figure 3:
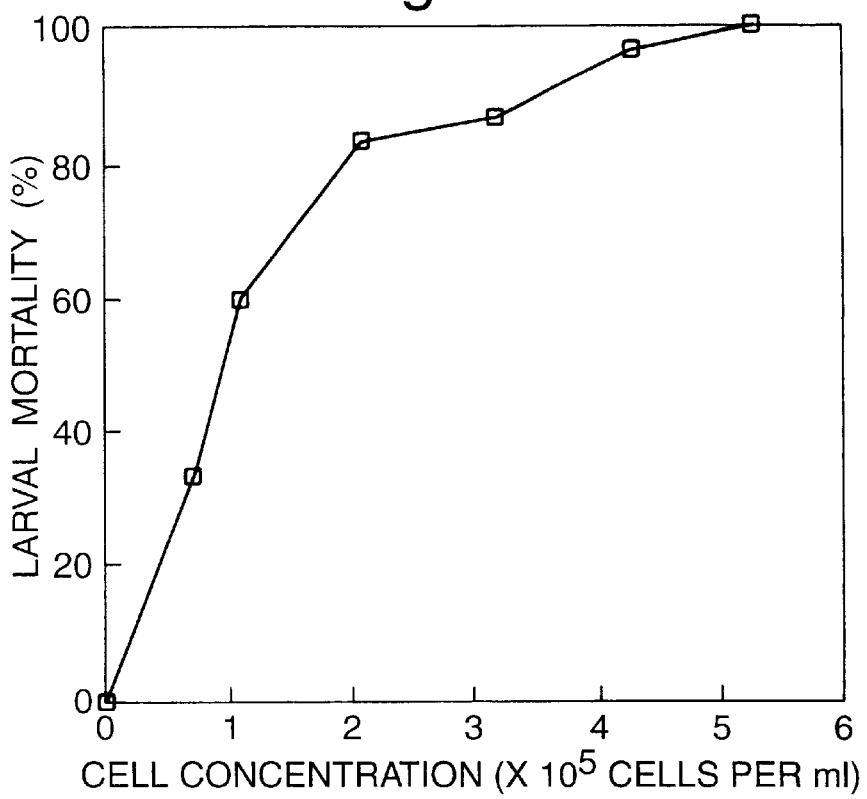

FIG. 3. Toxicities of CryIVADR expressed in cyanobacterium Anabaena PCC 7120 (clone #11) carrying pSBJ2 (FIG. 1). The cells of exponentially growing culture in $BG_{11}$ were centrifuged, and the pellets were suspended in distilled tap water and introduced at the indicated concentrations into 10 third-instar *A. aegypti* lavae in 50 ml. tap water. Mortality was recorded after 24h at 28° C.

EXAMPLE 1

As stated, a combination of CryIVA, CryIVD and p20, previously cloned and expressed in *E. coli* as an operon (in pHE4-ADR) as described by the present inventor and others (Mosquito larvicidal activity of *Escherichia coli* with combinations of genes from *Bacillus thuringiensis* sbsp. *israelensis*. J. Bacteriol. 177: 2,851–2,857., 1995), the teachings of which are incorporated herein by reference, was introduced into the nitrogen fixing filamentous Anabaena PCC 7120, and the most toxic clones selected for further studies.

a) Construction of shuttle vector for expression (FIG. 1)

The recombinant pHE4-ADR was found to contain a single KpnI site located downstream of CryIVA by KpnI/PstI double digestion (data not shown). This site was deleted to produce pHE4-ADR-K), necessary for further construction (below), by digesting pHE4-ADR with KpnI and filling the sticky ends with T4 polymerase to form blunt ends which were ligated by T4 DNA ligase. The other vector pBS-SK/N had been constructed to include a NcoI site by inserting 135 pb PstI-XhoI fragment from pUHE24-2 in the polylinker of pBlueScriptII SK$^+$ (Strategene Co. Startagene Catalog. La Jolla, Calif. 1994).

The CryIVADR operon was transferred from pHE4-ADR (-K) into pBS-SK/N by NcoI/PstI double digestion to produce pSBJ1, which was then united with pRL488p at their unique KpnI sites (above). This latter plasmid had been prepared by inserting 1 kb SalI-KpnI fragment containing the strong constitutive promoter $P_{psbA}$ from pRL435K into the shuttle vector pRL488 as described by J. Elhai, et. al. (Developmental regulation and spatial pattern of expression of the structural genes for nitrogenase in the cyanobacterium Anabaena. EMBO J. 9:3,379–3,388, 1990). The final construct (of 23.2 kb) with the CryIVADR operon under $P_{psbA}$ control was designated pSBJ2.

b) Introduction of pSBJ2 into Anabaena PCC 7120.

The recombinant shuttle expression vector pSBJ2 was introduced into Anabaena PCC 7120 by triparental mating with *E. coli* (according to the procedure described by J. Elhai, Conjugal transfer of DNA to cyanobacteria. Methods Enzymol. 167:747–754, 1988). *E. coli* HB101 harboring pSBJ2 and the helper plasmid pRL528 and *E. coli* J53 with the conjugal plasmid Rp4 were mixed with Anabaena PCC 7120 pregrown in $BG_{11}$ liquid medium at 28° C. without stirring under cool water fluorescent light illumination. The mixture was spread onto nitrocellulose membrane over $BG_{11}$ agar plates. After 24 h. of incubation, the membranes were transferred to selective plates with 25 µg ml$^{-1}$ neomycin and colonies formed on the membranes about 10 days later were inoculated into 5 ml $BG_{11}$ medium with 25 µg ml$^{-1}$ neomycin. After one week, when the true exconjugant clones could grow up, they were inoculated each into a flask and grown under the same conditions. Two clones (designated #7 and #11) among about 100 tested (below) were found toxic to larvae of *Aedes aegypti*. They were then freed of contamination *E. coli* by streaking on agar plates, and shown to grow well on $BG_{11}$ liquid medium with 50 µml$^{-1}$ neomycin, as measured by means of chlorophyll determination calorimetrically in methanol extracts. Growth of clone #11 is displayed in FIG. 2, with an initial innoculum of 1 µml$^{-1}$ chlorophyll.

EXAMPLE 2

Mosquito Larvicidal Activity (FIG. 3)

For bioassays, cells of *E. coli* or Anabaena PCC 7120, were cultivated in liquid media as usual, harvested by centrifugation and re-suspended in distilled water. Samples were added to 10 third instar larvae of *Aedes aegypti* in disposable cups with 50 ml sterile tap water, and larvicidal activity was determined after 24 h. at 28° C. The values of $LC_{50}$ (concentration of cells which kills 50% of exposed population in a standard bioassay) were determined by probit analyses with duplicated bioassays at each of six doses.

Two clones of Anabaena PCC 7120, #7 and #11, exhibited very high toxicity (99% mortality) against *Ae. aegypti* larvae, as did the *E. coli* strains harboring pSBJ2. The $LC_{50}$ clone #11 was $0.9 \cdot 10^5$ cells ml$^-$ (0.8 µg protein ml$^{-1}$), which is the lowest ever reached for engineered cyanobacterial cells with *B. thuringiensis* subsp. *israelensis* toxin genes.

EXAMPLE 3

Plasmid Rescue from Engineered (Clone #11) Anabaena PCC 7120

For analysis of plasmid stability in Anabaena cells, pSBJ2 was isolated from *E. coli* MRF' cells which had been transformed with total DNA of clone #11. Plasmids isolated from each of several *E. coli* colonies, selected on LB plates with ampicillin and kanamycin (50 µg ml$^{-1}$ of each), were found to be of the same size as pSBJ2. Cultures of *E. coli* transformed with the isolated plasmids were as toxic as the original clone (data not shown).

As will be realized the present invention provides for the first time in its most preferred embodiment transgenic Anabaena PCC 7120 with a combination of three δ-endotoxin genes (CryIVA, CryIVD, p20) of *B. thuringiensis* subsp. *israelensis* expressing mosquito larvicidal activity. In addition, according to the present invention it has now been found and proven for the first time, that this gene combination, previously expressed in *E. Coli* under an inducible promoter, expresses toxicity constitutively.

In contradistinction, as reported in the prior art, the cyanobacterium Agmenellum quadruplicatum PR-6, transformed with CryIVD behind its own strong phycocyanin promoter ($P_{cpcb}$), produced inclusion bodies and was mosquito larvicidal, but onset of toxicity to *C. pipiens* larvae, fed at 12 h. intervals right from hatching, was delayed, high mortality occurred only after six days as previously report by R. C. Murphy et. al. Cloning and expression of the CryIVD gene of *Bacillus thuringiensis* subsp. *israelensis* in the cyanobacterium Agmenellum quadruplicatum PR-6 and its resulting larvicidal activity Appl. Environ. Microbiol. 58:1,650–1,655 1992. Even though there were differences in using strains of cyanobacteria, promoters and assaying methods, the toxicity of the clones of the present invention of Anabaena PCC 7120 is surprisingly and unexpectedly much higher than those previously reported.

The high toxicity of this gene combination in Anabaena PCC 7120 as seen in FIG. 3 confirms the observed synergistic interactions between CryIVA and CryIVD in *E. coli*. Very low toxicity against larvae of *Ae. aegypti* and none against Culex quinquefasciatus of *E. coli* expressing CryIVD alone had indeed been observed and only detectable by immuno-blot analysis as 34 and 40 kDa proteolytic fragments. Each of the purified CryIVA and CryIVD was toxic to larvae of *Ae. aegypti, Anopheles stephensi* and *C. pipiens;* fed together, they demonstrate significant synergism against larvae of these three mosquito species.

It has also been found that cells carrying p20 produced substantially more CryIVD than did those without it. Thus, p20 seems to slightly and partially stabilize CryIVD.

Thus, the present invention provides a biocontrol agent comprising a combination of the genes CryIVA and CryIVD; and, a biocontrol agent comprising a combination of the genes CryIVA, CryIVD and p20.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A biocontrol agent against larvae of mosquitoes and blackflies comprising transgenic Anabaena PCC 7120 carrying a synergistic combination of the endotoxin genes CryIVA (cry4Aa) and CryIVD (cry11Aa) of *Bacillus thuringiensis* subsp. *israelensis*.

2. A biocontrol agent according to claim 1 comprising a combination of the genes Cry IVA (cry4Aa), CryIVD (cry11Aa) and a p20 δ-endotoxin gene of *B. thuringiensis* subsp. *israelensis*.

3. A plasmid that replicates in cyanobacteria comprising the endotoxin genes CryIVA (cry4Aa) and CryIVD (cry11Aa) of *Bacillus thuringiensis* subsp. *israelensis*.

4. The plasmid of claim 3 that further comprises a p20 δ-endotoxin gene of *B. thuringiensis* subsp. *israelensis*.

5. A cell comprising the plasmid of claim 3.

6. The cell of claim 5 that is a cyanobacterium.

7. The cell of claim 5 that is Anabaena PCC 7120.

8. A method for controlling mosquitos or black flies comprising contacting a mosquito or blackfly larva with a toxic amount of Anabaena PCC 7120 carrying the endotoxin genes CryIVA (cry4Aa) and CryIVD (cry11Aa) of *Bacillus thuringiensis* subsp. *israelensis*.

9. The method of claim 8 comprising contacting a larva of Aedes, Anopheles or Culex with a toxic amount of Anabaena PCC 7120 carrying the endotoxin genes CryIVA (cry4Aa) and CryIVD (cry11Aa) of *Bacillus thuringiensis* subsp. *israelensis*.

10. The method of claim 8 comprising contacting a blackfly larva with a toxic amount of Anabaena PCC 7120 carrying the endotoxin genes CryIVA (cry4Aa) and CryIVD (cry11Aa) of *Bacillus thuringiensis* subsp. *israelensis*.

11. A method for controlling mosquitos or black flies comprising contacting a mosquito or blackfly larva with a toxic amount the cell of claim 5.

12. A method for making a biocontrol agent against larvae of mosquitoes or blackflies comprising transforming Anabaena PCC 7120 with the endotoxin genes CryIVA and CryIVD of *Bacillus thuringiensis* subsp. *israelensis* and selecting a transformant toxic for a mosquito or blackfly larva.

13. The method of claim 12, further comprising culturing or growing said transformant in a suitable medium and harvesting said transformant in a form suitable for administration to mosquito or blackfly larva.

* * * * *